US009005127B2

(12) United States Patent
Azuma (10) Patent No.: US 9,005,127 B2
(45) Date of Patent: Apr. 14, 2015

(54) ULTRASOUND IMAGE PICKING-UP DEVICE (75) Inventor: Takashi Azuma, Kodaira (JP)

(73) Assignee: Hitachi Medical Corporation, Tokyo (JP)

( * ) Notice: Subject to any disclaimer, the term of this patent is extended or adjusted under 35 U.S.C. 154(b) by 849 days.

(21) Appl. No.: 12/663,547

(22) PCT Filed: Jan. 31, 2008

(86) PCT No.: PCT/JP2008/051566
§ 371 (c)(1),
(2), (4) Date: Dec. 8, 2009

(87) PCT Pub. No.: WO2008/149573
PCT Pub. Date: Dec. 11, 2008

(65) Prior Publication Data
US 2010/0174192 A1 Jul. 8, 2010

(30) Foreign Application Priority Data
Jun. 8, 2007 (JP) .................................. 2007-152889

(51) Int. Cl.
A61B 8/00 (2006.01)
A61B 5/05 (2006.01)
G06K 9/32 (2006.01)
A61B 8/14 (2006.01)
A61B 6/00 (2006.01)
A61B 8/08 (2006.01)
(Continued)

(52) U.S. Cl.
CPC . A61B 8/14 (2013.01); A61B 5/055 (2013.01); A61B 6/032 (2013.01); A61B 6/5247 (2013.01); A61B 8/463 (2013.01); A61B 8/469 (2013.01); A61B 8/5238 (2013.01); G01S 7/52092 (2013.01); G01S 15/8959 (2013.01); A61B 8/0816 (2013.01)

(58) Field of Classification Search
USPC ........... 600/437, 415, 443, 407; 382/128, 294
See application file for complete search history.

(56) References Cited

U.S. PATENT DOCUMENTS 5,720,287 A * 2/1998 Chapelon et al. ............. 600/439
6,290,648 B1 * 9/2001 Kamiyama ................... 600/443
(Continued)

FOREIGN PATENT DOCUMENTS

JP 56-116447 9/1981
JP 3-12137 1/1991
(Continued)

Primary Examiner — Katherine Fernandez
(74) Attorney, Agent, or Firm — Baker Botts L.L.P.

(57) ABSTRACT

There is provided an ultrasound image picking-up device that can correct a positional shift from a reference image before therapy even with insufficient clarity of an ultrasound image. An image processing system includes a position recognition device 1 for recognizing a position to be recognized of an object; a cross sectional image processor 6 that computes cross sectional image data of the object including position information of the position to be recognized; a probe 2 that transmits and receives ultrasound to the object; a ultrasonic image processor 3 that computes a plurality of ultrasound image data based on the ultrasound received by the probe 2; an image selector 7 that selects ultrasound image data including the area to be recognized from the plurality of ultrasound image data; an image processor 4 that aligns, in the area to be recognized, the cross sectional image data with the ultrasound image data including the area to be recognized; and a display 5 that displays a processing result of the image processor.

9 Claims, 11 Drawing Sheets (51) Int. Cl.
*G01S 7/52* (2006.01)
*A61B 5/055* (2006.01)
*A61B 6/03* (2006.01)
*G01S 15/89* (2006.01)

(56) References Cited

U.S. PATENT DOCUMENTS 7,204,254 B2 * 4/2007 Riaziat et al. .................. 128/897
7,421,647 B2 * 9/2008 Reiner ........................... 715/230
2004/0236193 A1 * 11/2004 Sharf ............................. 600/302
2007/0010743 A1 * 1/2007 Arai .............................. 600/443

FOREIGN PATENT DOCUMENTS

| | | |
|---|---|---|
| JP | 2006-25958 | 2/2006 |
| WO | WO 2004/098414 | 11/2004 |

* cited by examiner

3D Data Acquired before Surgery
(such as MRI or X-Ray CT)

Case Of Frequency Division

FIG. 10B

Case Of Code Division

FIG. 11A

Side View

FIG. 11B

Front View

ULTRASOUND IMAGE PICKING-UP DEVICE

TECHNICAL FIELD

The present invention relates to an ultrasound image picking-up device that displays an ultrasound cross sectional image.

BACKGROUND ART

An ultrasound diagnosis device as one of image diagnosis devices is easy to handle and can noninvasively observe an arbitrary cross section in real time, and is thus very widely used for diagnosis. Meanwhile, an ultrasound image picked up by the ultrasound diagnosis device is sometimes compared with a cross sectional image (hereinafter referred to as a reference image) picked up by a different image diagnosis device such as an X-ray CT device or an MRI device that more clearly visualizes shape information for comprehensive diagnosis.

Particularly, an MRI image can be picked up by various parameters (T1 enhancement, T2 enhancement, diffusion imaging, or the like), and information that is not included in the ultrasound image can be added. Thus, it is useful to compare a real-time ultrasound image with a previously picked-up reference image.

For example, Patent Document 1 describes a method of correcting a shift in correspondence between a reference image and an ultrasound image. It is proposed that the disclosed correcting method is performed to correct the shift while it is small even if the shift occurs during image pickup, and thus the reference image and the ultrasound image are used in an easily linked state.

Patent Document 1: JP Patent Application Publication No. 2005-506006

DISCLOSURE OF THE INVENTION

Problems to be Solved by the Invention

However, when ultrasound image picking-up of an inside of a cranium is performed from outside the cranium, attenuation of ultrasound in the cranium or the like causes insufficient sensitivity, and an ultrasound image picked up during therapy becomes unclear. There is an unsolved problem that with such an unclear image, it is difficult to correct a positional shift from a reference image before therapy caused with progress of the therapy.

The present invention has an object to provide an ultrasound image picking-up device that can correct a positional shift from a reference image before therapy even with insufficient clarity of an ultrasound image.

Means for Solving the Problems

An ultrasound image picking-up device of the present invention includes: an ultrasound probe that transmits and receives ultrasound to an object to which a position recognition device is mounted; an ultrasonic image processor that computes an ultrasound cross sectional image based on the ultrasound received by the ultrasound probe; an image data memory that stores previously acquired volume image data of the object; a data selector that selects desired slice image data from the volume image data of the object stored in the image data memory; a cross sectional image reconstruction processor that reconstructs a cross sectional image corresponding to the ultrasound cross sectional image based on the ultrasound transmitted and received by the ultrasound probe from the slice image data selected by the data selector; a controller that links a coordinate system of the ultrasound probe with a coordinate system of the volume image data; and a display that displays the aligned ultrasound cross sectional image and the cross sectional image reconstructed by the cross sectional image reconstruction processor in an associated manner.

The image data memory can store volume image data picked up by an X-ray CT device or an MRI device, and in the volume image data, position markers are placed in an expected arrangement position of the position recognition device and an expected arrangement position of the ultrasound probe. The controller aligns an ultrasound cross sectional image including an image showing the position recognition device computed based on the ultrasound transmitted and received by the ultrasound probe arranged in the expected position with a cross sectional image reconstructed by the cross sectional image reconstruction processor from the slice image data including the position marker selected by the data selector, using images of the position recognition device and images of the position markers included in the images.

As the position recognition device, a chip can be used that includes a transmitter and receiver and a signal processor, and transmits a signal according to receiving of the ultrasound from the ultrasound probe. A laser pointer can be used as a device that confirms a relative position between the position recognition device and the ultrasound probe.

A position sensor that detects motion of the ultrasound probe is provided, the data selector selects slice image data corresponding with a position of the ultrasound probe detected by the position sensor from the image data memory, and a cross sectional image reconstructed from the slice image data is displayed, and thus even if the ultrasound probe moves, the ultrasound cross sectional image and a reference image corresponding therewith can be displayed in an associated manner.

Advantage of the Invention

According to the ultrasound image picking-up device of the present invention, a positional shift from a reference image before therapy can be corrected even with insufficient clarity of an ultrasound image.

DESCRIPTION OF SYMBOLS

1 ... position recognition device
2 ... probe
3 ... ultrasonic image processor
4 ... controller
5 ... display
6 ... cross sectional image reconstruction processor
7 ... data selector
8 ... image data memory
9 ... position sensor
10 ... position detector
11 ... therapeutic system
12 ... probe position adjuster
13 ... laser diode
201 ... oscillator
202 ... amplifier
   203 ... transmission circuit
   204 ... ID input
   205 ... waveform memory
   206 ... A/D converter
   207 ... decision circuit
   208 ... D/A converter
   209 ... amplifier

BEST MODE FOR CARRYING OUT THE INVENTION

Now, an embodiment of the present invention will be described with reference to the drawings.

Figure 1:
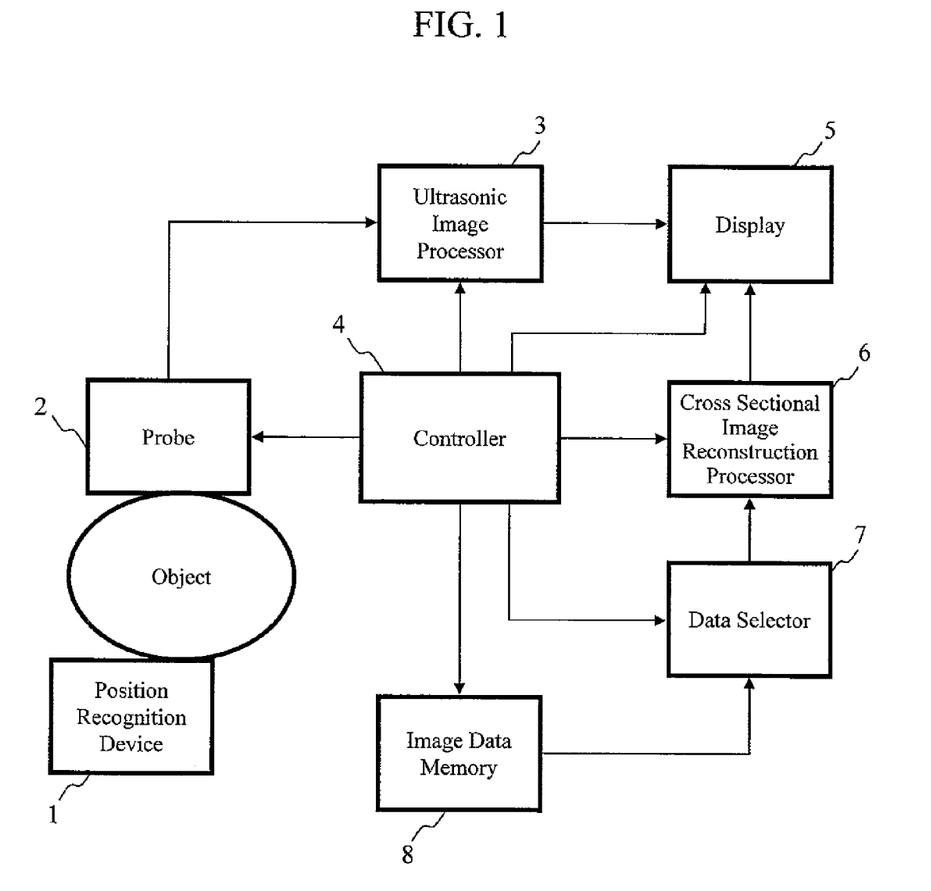
FIG. 1 is a block diagram of a device for carrying out the present invention.

FIG. 1 is a block diagram showing an example of an ultrasound image picking-up device according to the present invention. Herein, a head of a patient is envisaged as an object. First, a position recognition device 1 is fixed to the object. The position recognition device 1 can be recognized on an ultrasound cross sectional image picked up by the ultrasound image picking-up device, and for example, constituted by a transponder described later. The position recognition device 1 is preferably fixed in a position as distant as possible from a probe setting surface on the, object so as to increase estimated accuracy of a cross section position of an ultrasound probe 2. In terms of use for transcranial ultrasound image picking-up, the position recognition device 1 is preferably set on an outside on the side opposite to a probe setting position with a cranium therebetween. This is because, in the cranium, diploe that strongly scatters ultrasound is thin at temple areas, and thus one temple is used as the probe setting surface, and the position recognition device 1 is set on the other temple, thereby most greatly facilitating observation of the position recognition device 1. An ultrasonic pulse echo signal transmitted and received by the ultrasound probe 2 is subjected to known ultrasonic signal processing by an ultrasonic image processor 3, and displayed on a display 5 as a cross sectional image.

Figure 2:
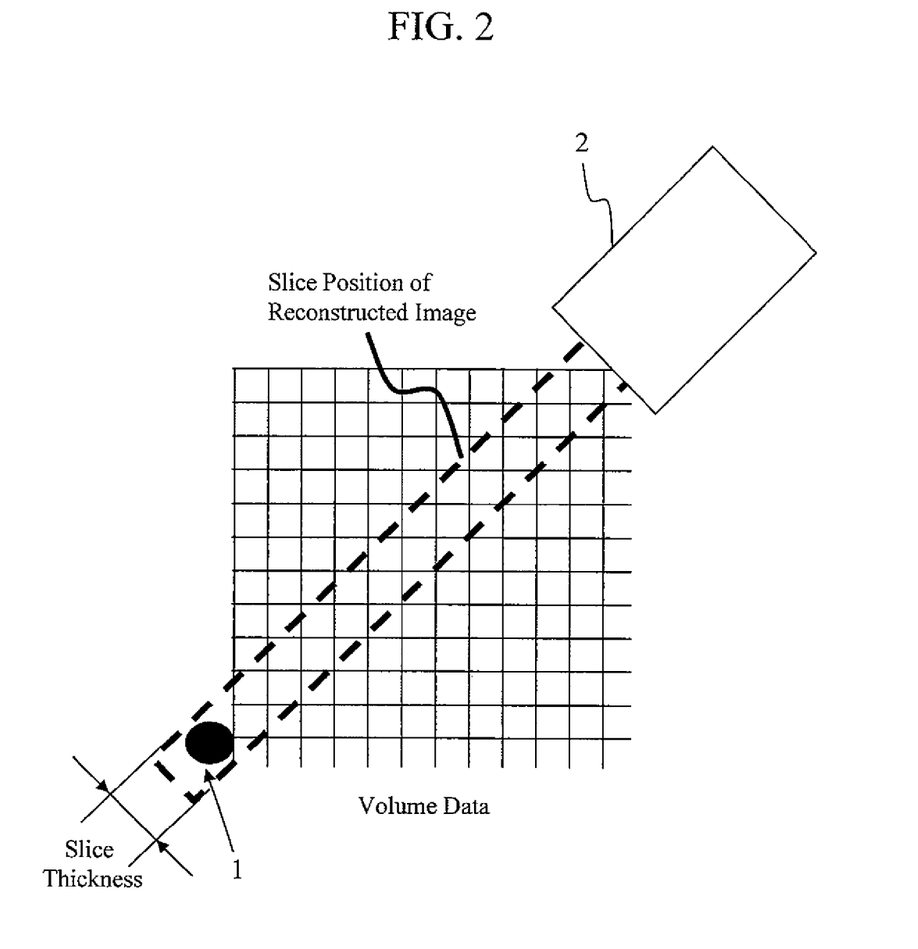
FIG. 2 illustrates volume data and a slice position of a reconstructed image.

In the present invention, a position of a cross section corresponding with the probe 2 and the position recognition device 1 is calculated from an image data memory 8 that stores multi-slice image data of an X-ray CT image or an MR image previously acquired, that is, three-dimensional volume data, a data selector 7 selects volume data (existing in a lattice point position in the drawing as brightness information) included in a limited slice thickness around the cross section as shown in FIG. 2, a cross sectional image reconstruction processor 6 performs scan conversion of a coordinate of a cross sectional image, and computes a reference image corresponding with the ultrasound cross sectional image. The reference image is displayed in an associated manner with the ultrasound cross sectional image, for example, side by side on a display 5. Herein, the images are referred to side by side, but when there is a limit such as a small screen region, the images may be switched and alternately displayed. Also, the images may be synthesized such as being added and displayed to facilitate alignment. Components of the device are operated under control by the controller 4.

The previously acquired X-ray CT image or MR image includes marks in the ultrasound probe setting position and the position recognition device setting position. For this purpose, when an X-ray CT image is used as three-dimensional volume data, position markers such as plastic tags are stuck to an ultrasound probe expected setting position and a position recognition device expected setting position in the object to pick up an X-ray CT image. When an MR image is used as three-dimensional volume data, position markers of lumps of fat or the like are stuck to the ultrasound probe expected setting position and the position recognition device expected setting position in the object to pickup an MR image. The probe position marker may be an anatomical feature point in the object. Thus, for the three-dimensional volume data stored in the image data memory 8 and the ultrasound cross sectional image picked up using the ultrasound probe, at least the probe setting position and the position recognition device setting position can be linked with each other.

Next, a method for linking positions of an ultrasound image during therapy and a reference image will be described using flowcharts in FIGS. 3 and 4. This process is performed by a processor 4. First, two coordinate systems, that is, a coordinate system of volume data for computing a reference image, and a coordinate system indicating the position of the ultrasound probe 2 are each initialized (S101). Then, the two coordinate systems are linked by a method described later (S102). When the coordinate systems are linked, a reference image corresponding with the position of the probe 2 can be computed (S103). When there is a positional shift in a state where the ultrasound image and the reference image are displayed side by side, the probe 2 is fixed to move the reference image or the reference image is fixed to move the probe 2 to adjust correspondence between the ultrasound image and the reference image so that the images are linked (S104). After the adjustment of the position is finished, a relative position between the coordinate system of the probe and the coordinate system of the volume data is fixed (S105). Then, a position sensor detects an amount of motion (translation and rotation) of the probe (S106), and the reference image is updated based on the motion of the probe (S107). A method of detecting the amount of motion of the probe will be described later.

Details of linking of the coordinate system of the probe with the coordinate system of the volume data (S102) that is particularly important in this process will be described with reference to FIG. 4. First, the link between the coordinate system of the reference image and the coordinate system of the probe is unlocked (S110). This is required in correcting the coordinate systems, and the coordinate systems are not originally linked immediately after the initialization of the coordinate systems. Then, a probe position marker in the reference image is searched (S111). Then, the ultrasound probe is set close to the probe position marker (S112). Thus, the ultrasound image necessarily includes the probe position on the image, and there is no need to search the probe position. Next, the position recognition device in the ultrasound image is searched (S113). The search herein may be a visual search by an operator, or automatic decision by the device when a calculation result of brightness or similarity to a preset specific waveform such as a cross correlation or a least squares method becomes a threshold for the device or more. Then, a position marker corresponding with the position recognition device is searched in the reference image (S114). Similarly, a second position recognition device and a position marker corresponding therewith are searched in the ultrasound image and the reference image (S115 and S116). As such, a correspondence can be obtained between a total of three points: one probe position marker and two position recognition devices (position markers), and thus the two cross sections of the ultrasound image and the reference image completely match each other. In this state, the link between the coordinate system of the reference image and the coordinate system of the probe is started (S117). When a patient noticeably moves during therapy and there is a possibility that the relative position between the position of the probe and an area for therapy moves, the process returns to the head of the flowchart in FIG. 4, and the coordinate system of the probe is linked with the coordinate system of the volume data.

Figure 3:
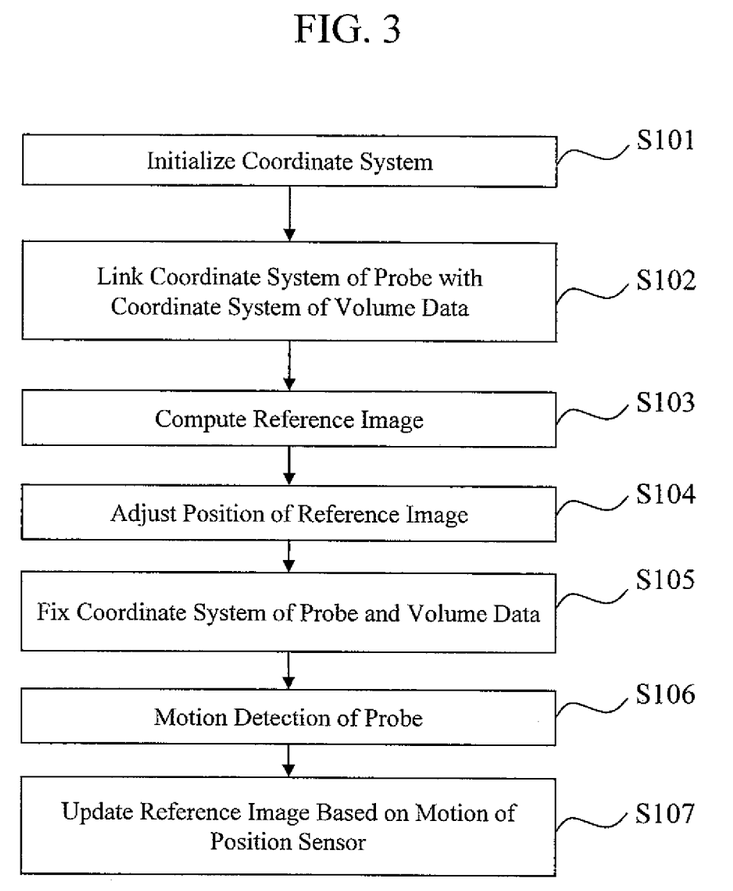
FIG. 3 is a flowchart for carrying out the present invention.
Figure 4:
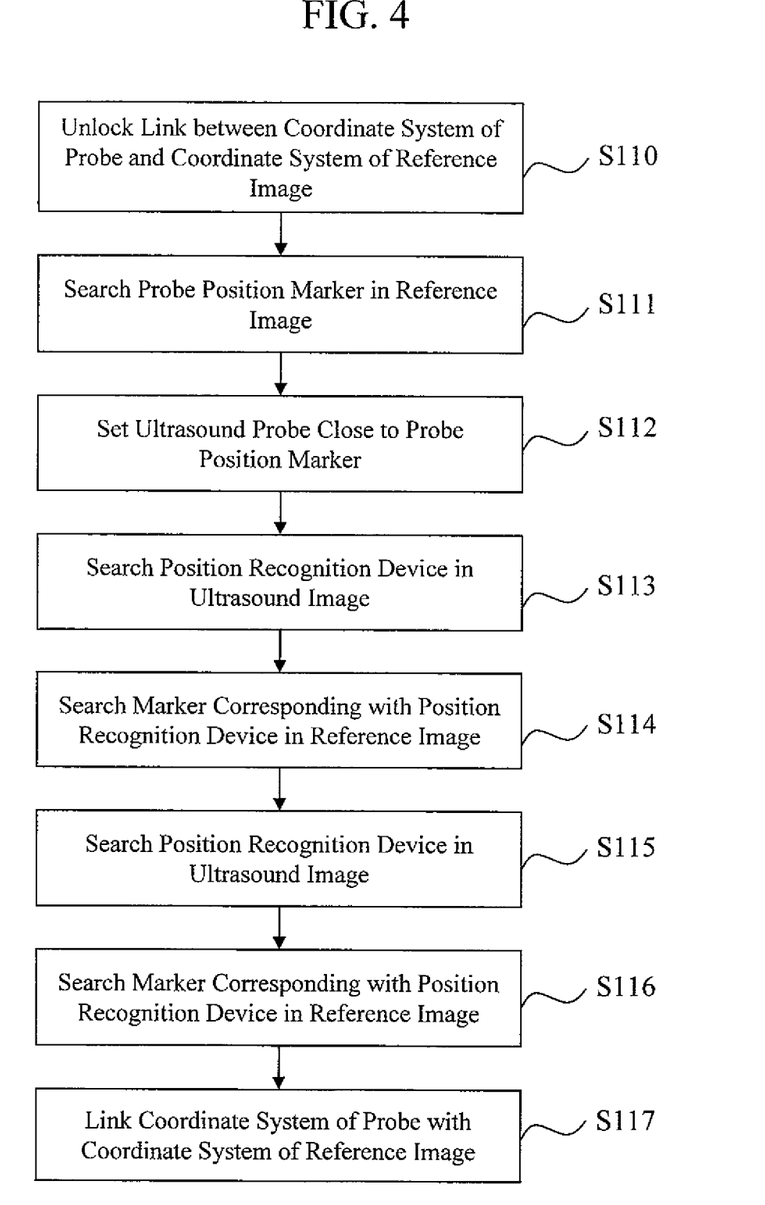
FIG. 4 is a flowchart for carrying out the present invention.
Figure 5:
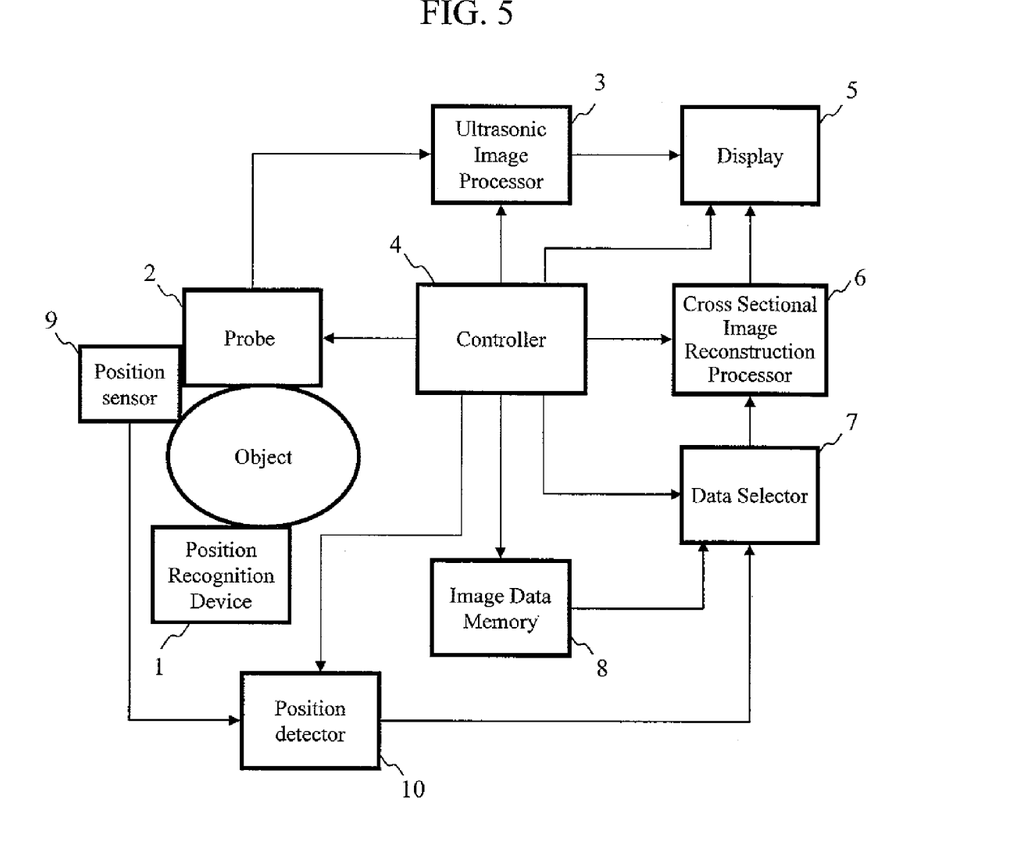
FIG. 5 is a block diagram of a device for carrying out the present invention.

There are some methods of motion detection of the probe in the flowchart in FIG. 3. In terms of a reduction in the number of components of a system, there is a method of comparing images picked up at different times to estimate motion of the probe position between the times. For example, cross correlation processing between image data picked up at one time and image data picked up at another time can be performed to estimate that the probe moves to a position with the highest correlation coefficient between the times. More conveniently, while the position of one image data is shifted, a difference between both the image data may be successively calculated to detect a position with a minimum difference and estimate that the probe moves by the positional shift. As the image data to be compared, part of the image data may be used or original receiving echo data of the image data may be used. In this case, there is no need for a sensor for detecting the position of the probe 2. However, particularly as in the present invention, when the sensitivity of the ultrasound image is not sufficiently high, accuracy of position estimation is also reduced. In such a case, as shown in FIG. 5, it is useful to use a position sensor 9 fixed to the probe 2. The position sensor 9 may be a gyroscope or an acceleration sensor, or a magnetic sensor used together with a transmitter. By any of these methods or a combination thereof, motion of the probe 2 through a total of 6 degrees of freedom: 3 degrees of freedom of translation and 3 degrees of freedom of rotation can be detected. Particularly, when the object and the ultrasound probe are fixed by some means as in transcranial ultrasonic therapy, all of the 6 degrees of freedom need not be detected, but motion detection of the probe and following of the reference image may be performed only for a degree of freedom of the most problematic motion.

Figure 6:
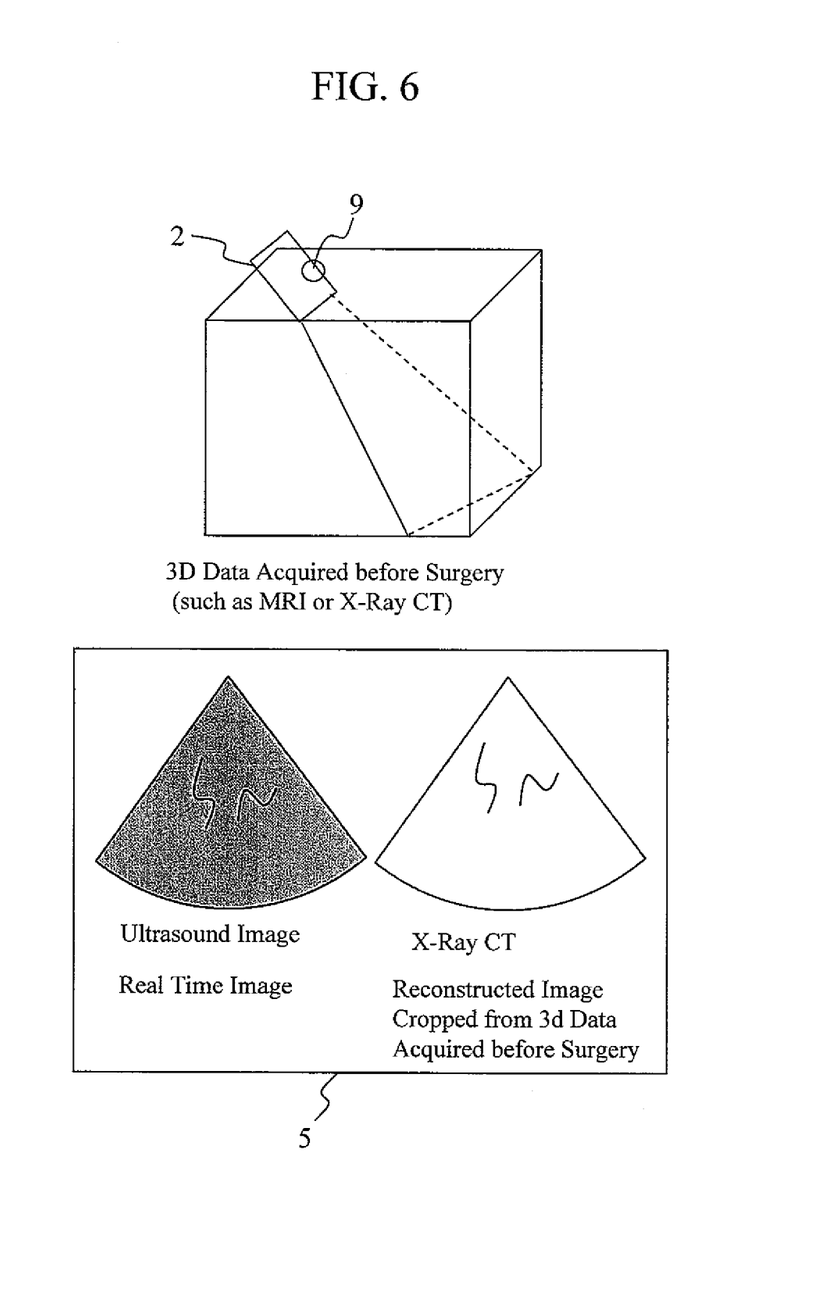
FIG. 6 illustrates a positional relationship between volume data and a probe and shows an example of image display on a display.
Figure 7:
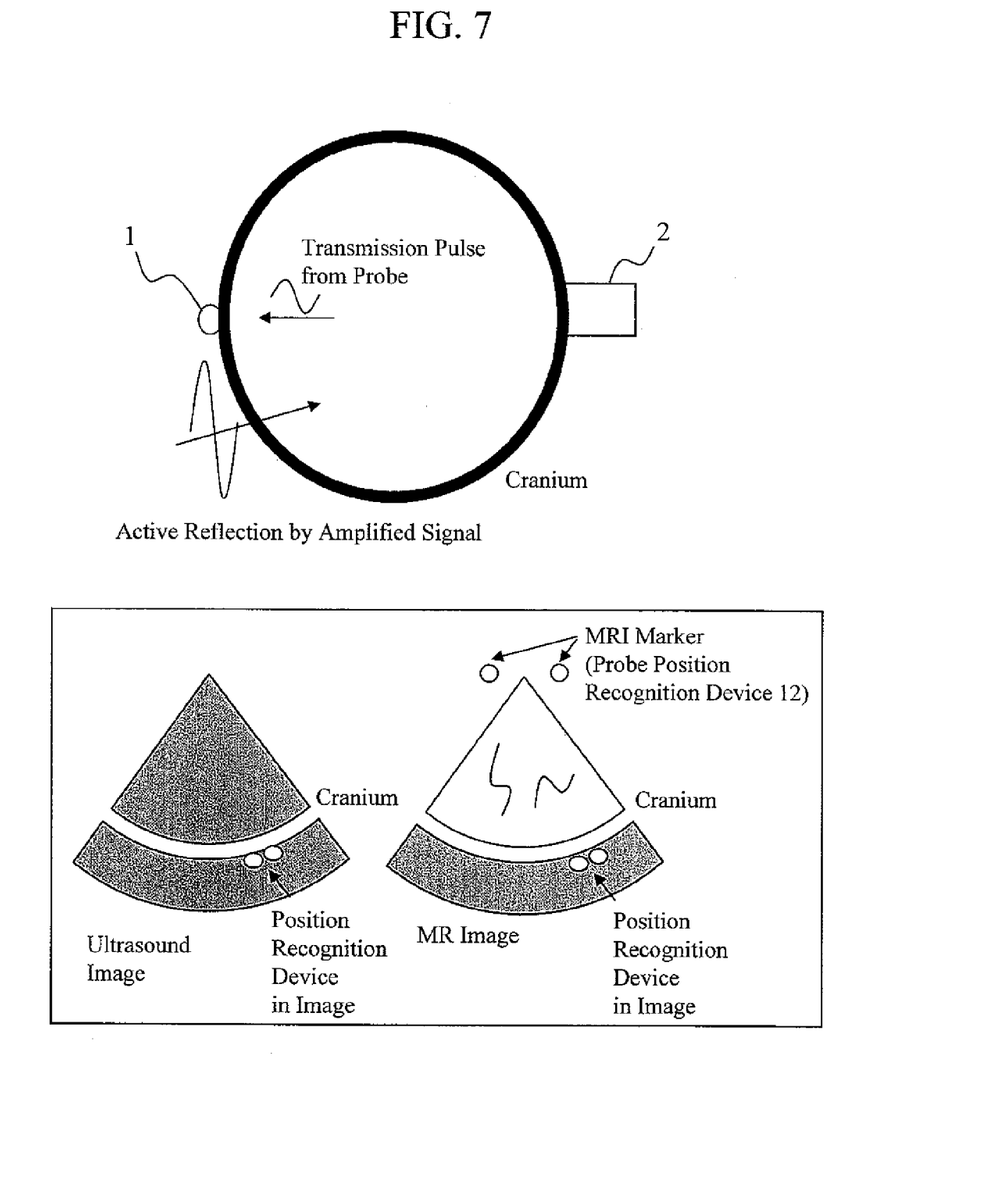
FIG. 7 illustrates a positional relationship between an object and the probe and shows an example of image display on the display.

Using the above-described method, as shown in FIG. 6, an image corresponding with an ultrasound image picking-up surface during therapy is computed from three-dimensional data such as an X-ray CT or MR image acquired before therapy, and displayed with an ultrasound cross sectional image acquired in real time side by side. Instead of displaying the images side by side, an image synthesized from two images may be displayed. In ultrasound image picking-up in a cranium, a state of diploe or a state of bones other than the diploe differs depending on patients, thus sensitivity of the ultrasound image significantly differs, and the real-time ultrasound image does not satisfactorily appear in the display 5 in some cases. In such cases, in the present invention, the position recognition device 1 can be used to increase alignment accuracy as shown in FIG. 7. The position recognition device 1 is preferably constituted by an electronic device called a transponder.

Figure 8A:
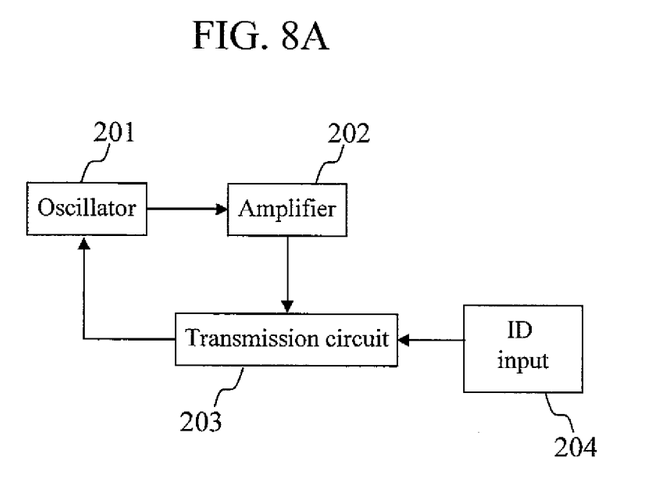
FIGS. 8A and 8B are configuration diagrams of a transponder.
Figure 8B:
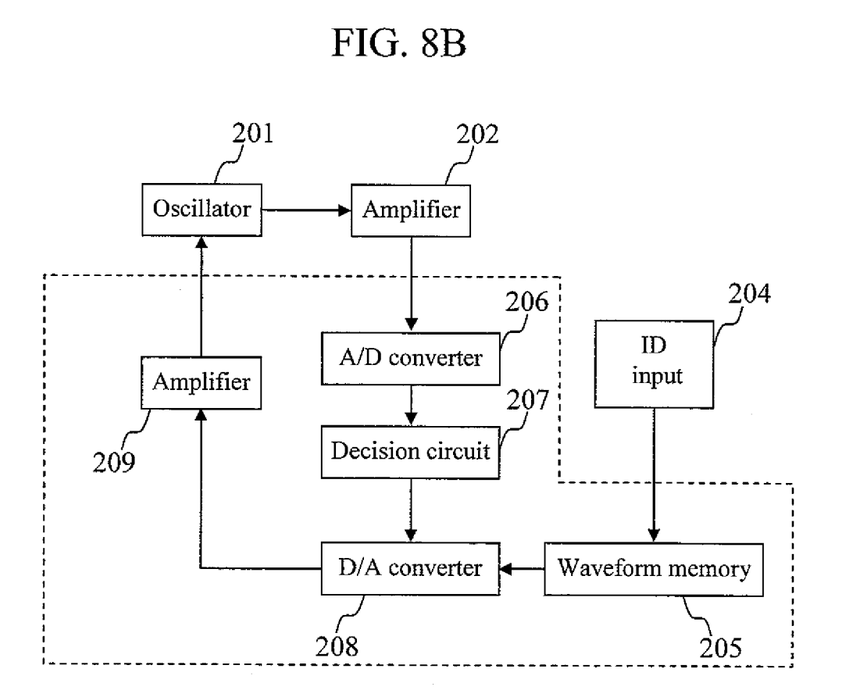

As shown in FIGS. 8A and 8B, the transponder includes a receiver, an amplifier 202, a transmission circuit 203, a recognition portion (ID input) 204, and a transmitter so as to receive an ultrasonic pulse and then immediately transmit the ultrasonic pulse. Generally, the receiver and the transmitter are the same oscillator 201. FIG. 8A shows an example of a transponder using an analog circuit, and FIG. 8B shows an example of a transponder using a digital circuit. The transmission circuit 203 in FIG. 8A includes an A/D converter 206, a decision circuit 207, a D/A converter 208, a waveform memory 205, and an amplifier 209 in FIG. 8B. Particularly, when a plurality of transponders are used, the transponders need to be differentiated, and thus the ID input 204 of the transponder is required. However, as described later, when the plurality of transponders are placed in a specific arrangement to improve recognition, ID is sometimes provided by an arrangement method. Herein, as a method of reducing a size of an oscillator including a circuit, a method of using an ultrasound oscillator using a semiconductor film such as a capacitive micromachined ultrasound transducer (cMUT) is also useful. The cMUT is a device that forms a gap held between upper and lower electrodes on a semiconductor substrate, applies a DC bias between the upper and lower electrodes, and causes oscillation using a Coulomb force applied between accumulated charges, and has a feature that the device can be formed by a semiconductor process such as silicon, and thus a circuit such as a preamplifier can be monolithically included as compared with a conventional oscillator of piezoelectric ceramics or the like.

Such an active reflector can be used to increase signal strength and signal specificity as compared with a passive reflection echo. To increase the signal specificity means to perform transmission with a different frequency from a received signal or specific coding even with the same frequency so that a signal from the transponder can be specifically recognized among signals having entered the ultrasound probe. The coding herein is a method in which, when a method of generally transmitting with one pulse is expressed by transmission with a signal of +1, a plurality of pulse sequences (pulse interval is, for example, time interval of inverse of transmission frequency) arranged on a time base, for example, +1, +1, −1, −1, +1, −1 are used, and received signals including the pulse sequences are displayed as one point using a filter for specific compression on a time base (autocorrelation function of the pulse sequences, or deformed function of the autocorrelation function such as a mismatched filter).

Figure 9:
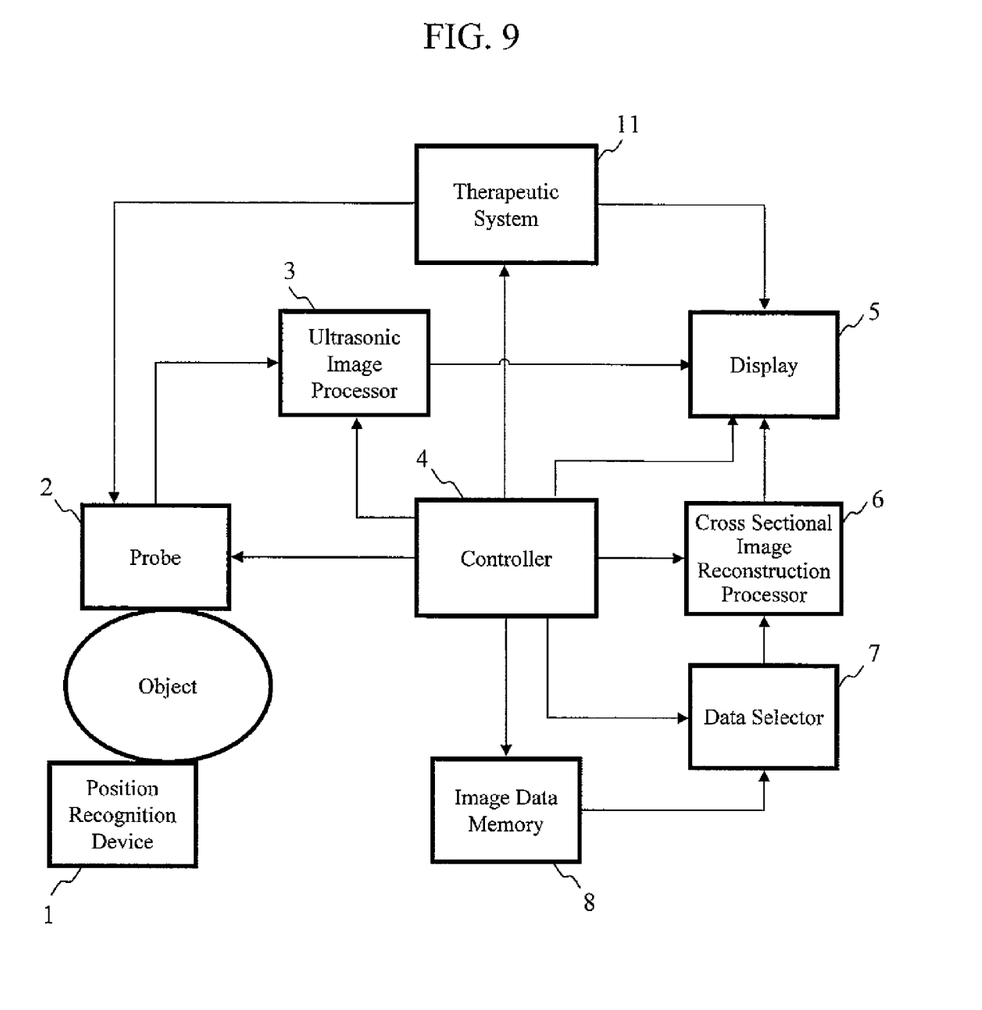
FIG. 9 is a block diagram of a device for carrying out the present invention.

As shown in a lower drawing in FIG. 7, displaying the ultrasound image when only the transponder is displayed on the left ultrasound image is important in the following respects. In transcranial ultrasonic therapy as shown in FIG. 9, a relative positional relationship between an imaging probe and a therapeutic probe is fixed, and thus even if the ultrasound image does not appear, a coordinate of the ultrasound probe is clear and a therapy target position can be properly navigated. In FIG. 9, a therapeutic system 11 controls a therapeutic ultrasound transmitting transducer included in the ultrasound probe 2. This method is effective for using a transponder for precise alignment when skinfold thickness or gas in a lung or an intestinal tract prevents imaging if not for an extreme case such as transcranial therapy. A feature point used in correspondence between a general image before surgery and an ultrasound image is as distant from the ultrasound probe as possible to increase accuracy in deciding the position of the ultrasound image picking-up surface. However, there is a trade-off such that the distant feature point is hard to recognize on the ultrasound image, leading to prevention of the increase in the positional accuracy. Thus, the active reflection such as the transponder can be used to avoid the trade-off. With the transponder, the transponder is placed on a back of a human object when the probe is applied to an abdomen, or the transponder is set in a position via the lung or the intestinal tract in a blind spot of the ultrasound image other than ultrasound in the cranium, thereby increasing accuracy in image alignment.

In ultrasound thrombolysis, a method can be proposed using different frequencies of 2 MHz for imaging and 500 kHz for increasing an effect of a thrombolytic agent. This is because spatial resolution is to be increased for imaging, while the frequency should not be increased for therapy to prevent an excessive increase in temperature of brain tissue. When such two different frequencies are used, an effect of using an image before surgery for navigation as in the present invention is particularly increased. This is because even if a picture does not appear in imaging, ultrasound having a lower frequency and higher penetration can be used for therapy. When the configuration in which the two frequencies can be used is positively used, for the transmission ultrasound from the transponder, a frequency band for therapy rather than for imaging can be used to increase sensitivity of position detection of the transponder.

For such a transponder, one transponder may be used for at least one place, but only one transponder sometimes provides insufficient specificity. In that case, as shown in the lower drawing in FIG. 7, a plurality of transponders are arranged in one place, and specificity is provided to the arrangement pattern, thereby increasing signal specificity from the transponder. If one image pickup surface is aligned with a reference image, a total of three points: the probe position and two recognition positions are sufficient. However, moving the probe to a reference position correction position different from a target position for each positional shift is troublesome, and thus it is useful that three or more position recognition devices are set and position correction is performed in a position closest to an image pickup surface including an area for therapy. At this time, signals from the transponder of the position recognition device need to be individually changed. The signals may be changed by the arrangement manner, or the frequency, or the coding method. The spatial arrangement, the frequency, or the coding method of the plurality of transponders (chips) may be combined.

Figure 10A:
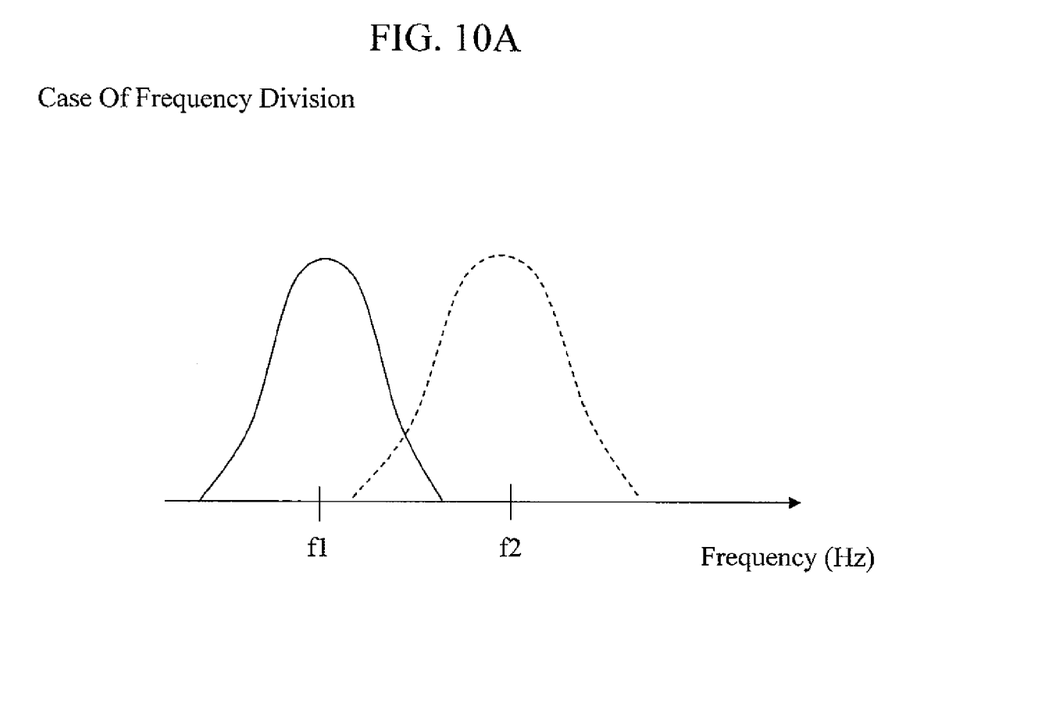
FIGS. 10A and 10B illustrate frequency bands of a signal from the transponder.
Figure 10B:
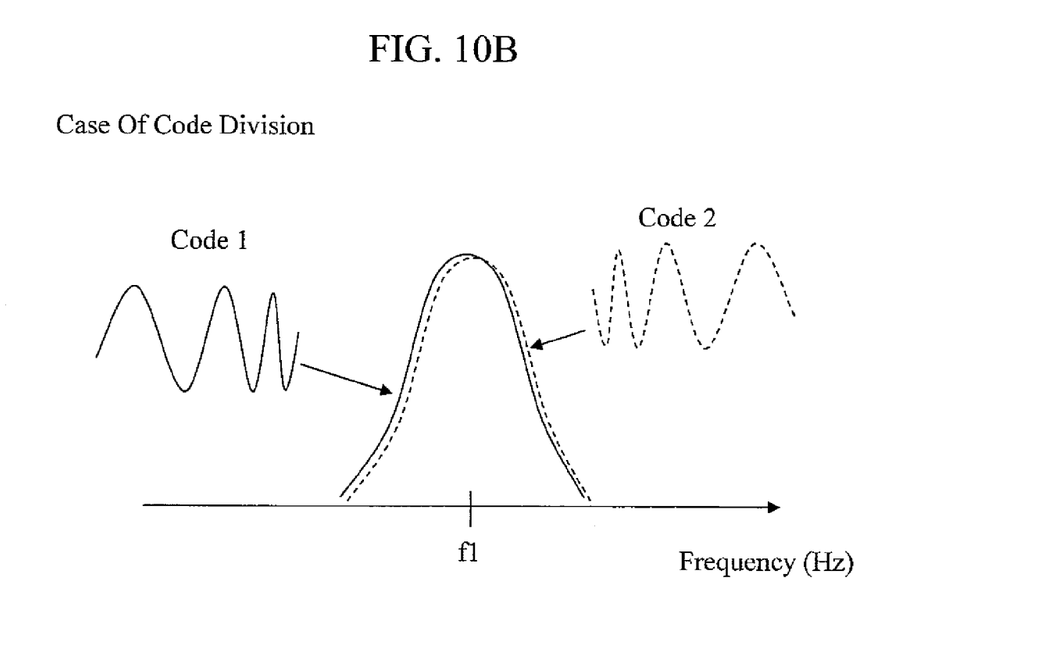

To increase the spatial resolution on the position of the transponder, the signal from the transponder needs to be broadband. However, to improve division between the plurality of transponders, it is necessary to prevent bands from overlapping as much as possible. For example, as shown in FIG. 10A, it is preferable to divide the bands without overlapping such that a frequency band f1 of a transponder 1 is 1 to 2 MHz, and a frequency band f2 of a transponder 2 is 2 to 4 MHz. However, in this case, there is an influence of frequency proportional damping or frequency dependency of transmittance that depends on bone thickness resonance when transmitting bones, and thus the frequency band is preferably the same in some cases. In such cases, as shown in FIG. 10B, coding signals that have the same frequency band but can be differentiated may be used for division as a useful method. Also, as another method for division with the same frequency band, as shown in FIG. 7, a plurality of transponders may be arranged for one recognition portion to allow differentiation of recognition portions by a manner of spatial arrangement. Such a method of providing spatial distribution facilitates differentiation from noise as compared with the method with one transponder, and is a very effective method.

As described above, according to the present invention, even with insufficient sensitivity of an ultrasound image such as in ultrasound image picking-up in a cranium, a positional shift can be corrected during use of a reference image before therapy. This increases positional accuracy of therapeutic ultrasound irradiation, and increases safety of therapy.

Figure 11A:
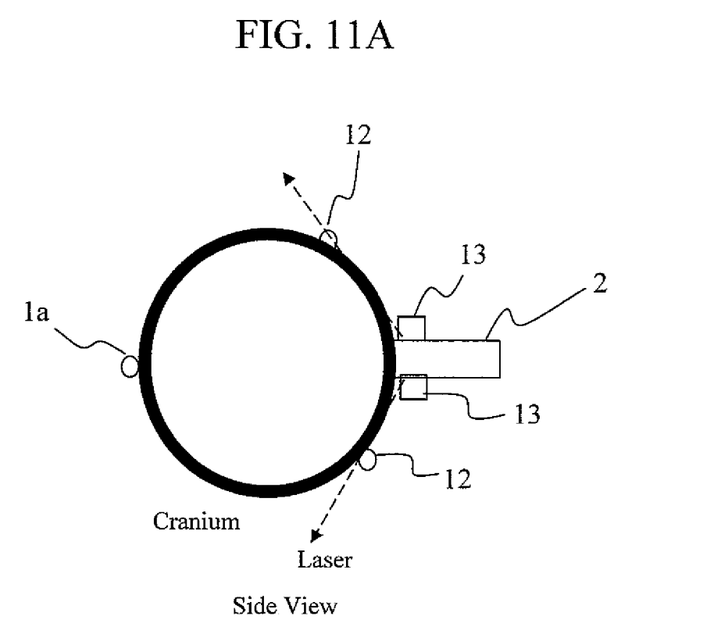
FIGS. 11A and 11B illustrate a positional relationship between an object and a probe.
Figure 11B:
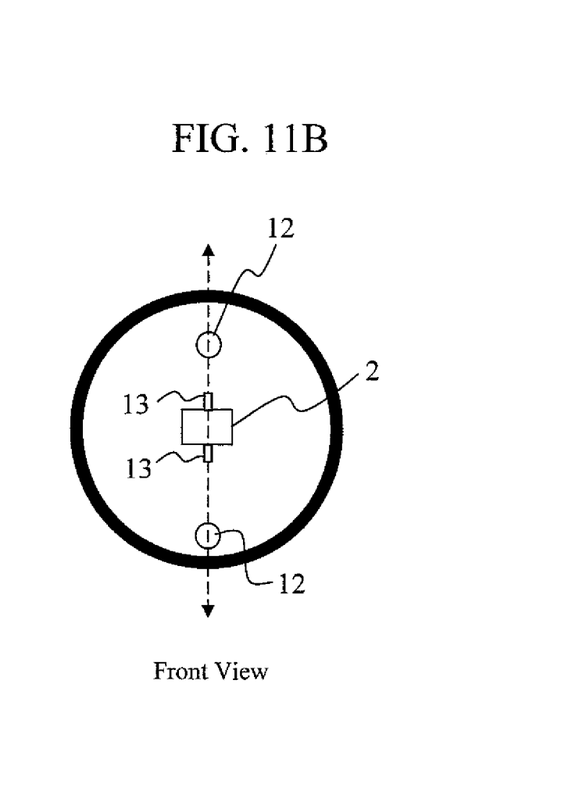

Also, as another embodiment, a probe position and a probe position deciding marker are not aligned with points but may be aligned with lines to facilitate alignment thereafter. This will be described with reference to FIGS. 11A and 11B. FIG. 11A is a side view and FIG. 11B is a front view. Position recognition devices 12 are arranged on positions easily seen from a setting surface side of the probe 2. Meanwhile, on the ultrasound probe 2, a laser diode 13 is set at an angle shown in FIG. 11A so that an image pickup surface of the ultrasound probe is displayed as a line on the object. To display the image pickup surface as a line, the laser diode may be moved along a line to be displayed, or a lens displaying a line such as a cylindrical lens may be used. The ultrasound probe 2 is set so that the laser line overlaps the positions of the position recognition devices 12, thereby facilitating linking between an ultrasound image and a reference image. As described above, a position recognition device 1a such as a transponder is set to detect the position, thereby allowing alignment with higher accuracy. In acquiring the reference image, it is preferable to stick many position markers to the position of the probe 2, the positions of the position recognition devices 1a and 12, or the like to pickup an X-ray CT image or an MR image for increasing alignment accuracy.

The invention claimed is:
1. An ultrasound image picking-up device comprising:
an ultrasound probe configured to transmit ultrasound to an object and to receive ultrasound from said object to which a position recognition device is mounted;
an ultrasonic image processor configured to compute an ultrasound cross sectional image based on the ultrasound received by said ultrasound probe;
an image data memory configured to store previously acquired volume image data of the object in which position markers are placed in an expected arrangement position of said position recognition device and an expected arrangement position of said ultrasound probe;
a data selector configured to select desired slice image data from the volume image data of the object stored in said image data memory;
a cross sectional image reconstruction processor configured to reconstruct a cross sectional image corresponding to the computed ultrasound cross sectional image from the slice image data selected by said data selector;
a controller configured to link coordinates of the ultrasound cross sectional image, which shows a position of said position recognition device computed based on the ultrasound received by the ultrasound probe arranged in said respective expected arrangement position, with coordinates of the reconstructed cross sectional image, which includes said position markers, based on a correspondence between said position recognition device in said ultrasound cross sectional image and said position markers in said reconstructed cross sectional image; and
a display configured to display the ultrasound cross sectional image and the reconstructed cross sectional image whose coordinates are linked in an associated manner,
wherein said position recognition device includes at least one chip that includes a transmitter and receiver for an ultrasonic pulse and a signal processor, wherein said transmitter transmits a coded ultrasonic pulse in response to said receiver receiving an ultrasonic pulse from said ultrasound probe in order to actively reflect the position of the position recognition device, and wherein said ultrasonic image processor is further configured to recognize a signal transmitting the position of the position recognition device based on the coded ultrasonic pulse from said position recognition device.

2. The ultrasound image picking-up device according to claim 1, further comprising a laser pointer configured to confirm a relative position between said position recognition device and said ultrasound probe.

3. The ultrasound image picking-up device according to claim 1, further comprising a position sensor configured to detect motion of said ultrasound probe, and said data selector selects slice image data corresponding with a position of said ultrasound probe detected by said position sensor from said image data memory.

4. The ultrasound image picking-up device according to claim 1, wherein said display is configured to display the ultrasound cross sectional image of the object and the signal transmitting position from the chip.

5. The ultrasound image picking-up device according to claim 1, wherein said image data memory stores volume image data picked up by an X-ray CT device or an MRI device.

6. The ultrasound image picking-up device according to claim 1, wherein said position recognition device is a combination of a plurality of chips that each include a transmitter and receiver and a signal processor, and each transmit signals according to receiving of the ultrasound from said ultrasound probe, and said ultrasonic image processor is configured to recognize the signal transmitting the position of said position recognition device by at least one of spatial arrangement, a frequency, or a coding method of said plurality of chips.

7. The ultrasound image picking-up device according to claim 1, wherein said ultrasound probe includes a transmitter configured to transmit therapeutic ultrasound.

8. The ultrasound image picking-up device according to claim 7, wherein a relative position of said ultrasound probe from said position recognition device is calculated, and a target position of said ultrasound probe in transmitting therapeutic ultrasound is guided based on the calculated relative position of said ultrasound probe.

9. The ultrasound image picking-up device according to claim 1, wherein said controller is further configured to display, in an associated manner, said ultrasound cross sectional image and said cross sectional image aligned, by at least one display mode of parallel display of the images, switching display of the images, or display of the images synthesized.

* * * * *